US011360075B2

(12) United States Patent
Bainbridge et al.

(10) Patent No.: US 11,360,075 B2
(45) Date of Patent: Jun. 14, 2022

(54) COLLECTING COMPONENTS OF A FLUID

(71) Applicant: Terumo BCT, Inc., Lakewood, CO (US)

(72) Inventors: Marlene Bainbridge, Golden, CO (US); Todd Curtis Green, Lakewood, CO (US); Logan Fender, Lakewood, CO (US)

(73) Assignee: TERUMO BCT, INC., Lakewood, CO (US)

( * ) Notice: Subject to any disclaimer, the term of this patent is extended or adjusted under 35 U.S.C. 154(b) by 0 days.

(21) Appl. No.: 16/812,552

(22) Filed: Mar. 9, 2020

(65) Prior Publication Data

US 2020/0209216 A1    Jul. 2, 2020

Related U.S. Application Data

(62) Division of application No. 15/783,866, filed on Oct. 13, 2017, now Pat. No. 10,585,085.
(Continued)

(51) Int. Cl.
*B04B 5/04* (2006.01)
*G01N 33/49* (2006.01)
(Continued)

(52) U.S. Cl.
CPC ......... *G01N 33/491* (2013.01); *A61M 1/3693* (2013.01); *A61M 1/3696* (2014.02);
(Continued)

(58) Field of Classification Search
CPC .............. A61M 1/3693; A61M 1/3696; A61M 2202/0021; A61M 2202/0427;
(Continued)

(56) References Cited

U.S. PATENT DOCUMENTS 4,968,295 A    11/1990   Neumann
5,674,173 A    10/1997   Hlavinka et al.
(Continued)

FOREIGN PATENT DOCUMENTS

DE    19728089 A1    1/1999
EP     2476447 A1    7/2012
(Continued)

OTHER PUBLICATIONS

International Search Report and Written Opinion, PCT/US2017/056658, dated Jan. 2, 2018.
(Continued)

*Primary Examiner* — Timothy C Cleveland
(74) *Attorney, Agent, or Firm* — Sheridan Ross P.C.

(57) ABSTRACT

Embodiments are described for separating/collecting components from a multi-component fluid such as whole blood. Some embodiments provide for controlling the amount of a component, such as platelets, introduced into a separation chamber to ensure that the density of fluid in the separation chamber does not exceed a particular value. This may provide for collecting purer components. Other embodiments may provide for determining a chamber flow rate based on a concentration of a component in the multi-component fluid, which may then be used to determine a centrifuge speed, to collect purer concentrated components.

20 Claims, 11 Drawing Sheets

Related U.S. Application Data

(60) Provisional application No. 62/407,607, filed on Oct. 13, 2016.

(51) Int. Cl.
    *A61M 1/36*     (2006.01)
    *B01D 21/24*     (2006.01)
    *B01D 21/26*     (2006.01)
    *B01D 21/34*     (2006.01)

(52) U.S. Cl.
    CPC ....... *B01D 21/2472* (2013.01); *B01D 21/262* (2013.01); *B01D 21/34* (2013.01); *B04B 5/0442* (2013.01); *A61M 2202/0021* (2013.01); *A61M 2202/0427* (2013.01); *A61M 2202/0439* (2013.01); *A61M 2205/3334* (2013.01); *B01D 2221/10* (2013.01); *B04B 2005/0471* (2013.01)

(58) Field of Classification Search
    CPC .. A61M 2202/0439; A61M 2205/3334; B01D 21/2472; B01D 21/262; B01D 21/34; B01D 2221/10; B04B 5/0442; B04B 2005/0471; G01N 33/491
    See application file for complete search history.

(56) References Cited

U.S. PATENT DOCUMENTS

| | | |
|---|---|---|
| 5,906,570 A | 5/1999 | Langley et al. |
| 5,939,319 A | 8/1999 | Hlavinka |
| 6,022,306 A | 2/2000 | Dumont et al. |
| 6,053,856 A | 4/2000 | Hlavinka |
| 6,334,842 B1 | 1/2002 | Hlavinka et al. |
| 7,963,901 B2 | 6/2011 | Langley et al. |
| 8,852,140 B2 | 10/2014 | Barry et al. |

FOREIGN PATENT DOCUMENTS

| | | |
|---|---|---|
| WO | 96/33023 A1 | 10/1996 |
| WO | 99/12590 A1 | 3/1999 |

OTHER PUBLICATIONS

Notice of Reasons for Refusal, Japanese Patent Application No. 2019-520011, dated Apr. 6, 2021. (English language translation included.).

COLLECTING COMPONENTS OF A FLUID

CROSS-REFERENCE TO RELATED APPLICATION(S)

This patent application is a divisional application of and claims priority to, U.S. patent application Ser. No. 15/783,866, entitled "COLLECTING COMPONENTS OF A FLUID," filed on Oct. 13, 2017. U.S. patent application Ser. No. 15/783,866 claims priority to U.S. Provisional Patent Application Ser. No. 62/407,607, entitled "COLLECTING COMPONENTS OF A FLUID," filed Oct. 13, 2016 and hereby incorporated by reference in its entirety as if set forth herein in full.

BACKGROUND

Separation processes are commonly used to isolate components of multi-component fluids in a variety of technology areas. For example, blood components are often separated from whole blood for transfusion or therapeutic purposes. Apheresis is one example of a blood separation process in which components are separated from whole blood.

In some separation processes, the purity of the components being separated from a multi-component fluid may be important. For example, some apheresis processes are performed to collect a target component from blood, e.g., platelets, for later therapeutic use(s). In these separation processes, it may be important to collect as much of the target component (e.g., platelets) as possible with as little of the other components (e.g., white blood cells) as possible. Providing mechanisms in the separation process to control the purity of a target component being collected may be useful.

Additionally, separation processes, such as an apheresis process may be performed on a donor in real time. It may therefore be preferable to a donor to have the process completed as quickly as possible. There is therefore a need to perform separation processes that are efficient and collect a component product that is as free of other components as possible.

Embodiments of the present invention have been made considering these and other considerations. However, the problems discussed above do not limit the applicability of the embodiments of the present invention to other applications.

SUMMARY

The summary is provided to introduce aspects of some embodiments of the present invention in a simplified form, and is not intended to identify key or essential elements of the claimed invention, nor is it intended to limit the scope of the claims.

Embodiments provide for methods of separating and/or collecting components of a fluid. Methods may provide for receiving, by at least one processor, first data related to an amount of a first component in a multi-component fluid. An adjustment to be used may be determined based on the first data. The multi-component fluid may then be introduced into a separation vessel to generate a composite fluid with components of the multi-component fluid. The composite fluid may then be separated into at least a first component and a second component in a separation chamber. During the separation, a concentration of at least one of the first component and/or the second component in the separation chamber may be maintained below a predetermined amount. The first component may then be collected in a storage container. In embodiments, the multi-component fluid may comprise whole blood. In some embodiments, the first component may comprise platelets with the first data comprising a platelet count.

Other embodiments may provide for a method of separating and/or collecting components of a biological fluid. Embodiments may provide for receiving first data related to a first amount of a first component in a first multi-component fluid from a first source. A first flow rate may then be determined based on the first data. A first centrifuge speed based on the first flow rate may then be determined. A centrifuge is then rotated at the first centrifuge speed. A flow of a first composite fluid that includes at least the first component of the first multi-component fluid and a second component of the first multi-component fluid is introduced into a first separation chamber. The first composite fluid may be separated from the first multi-component fluid. In the separation chamber, the first component of the first composite fluid may be separated from the second component of the first composite fluid by subjecting the first composite fluid while in the first separation chamber to a centrifugal field of a first strength created by the centrifuge rotating at the first centrifuge speed. The first component of the first composite fluid may then be collected in a first storage container.

BRIEF DESCRIPTION OF THE DRAWINGS

Non-limiting and non-exhaustive embodiments are described with reference to the following figures.

DETAILED DESCRIPTION

The principles of the present invention may be further understood by reference to the following detailed description and the embodiments depicted in the accompanying drawings. It should be understood that although specific features are shown and described below with respect to detailed embodiments, the present invention is not limited to the embodiments described below.

Embodiments below may be described with respect to processing biological fluids with particulate components (e.g., cells) to separate and/or collect a component. For example, the embodiments may be described with respect to separating whole blood into components (e.g., red blood cells, white blood cells, platelets, and plasma). However, this is done simply for illustrative purposes. It is noted that the embodiments are not limited to the description below. The embodiments are intended for use in products, processes, devices, and systems that process organic or inorganic particles, particulates, agglomerates. Accordingly, embodiments are not limited to separation or concentration of blood components, but may be used to separate, concentrate, and or collect any particle from any fluid.

Figure 1:
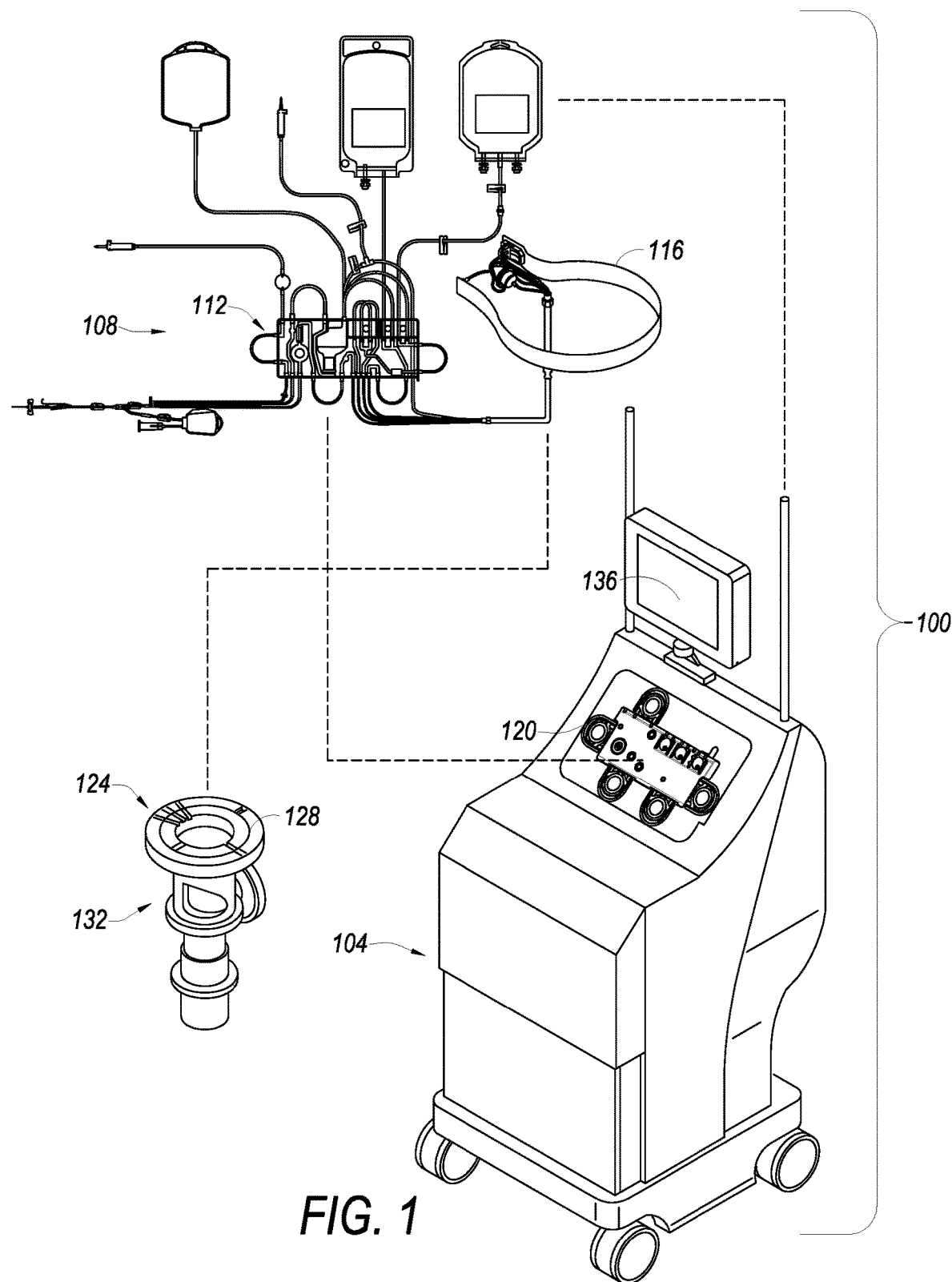
FIG. 1 illustrates a separation system that may be used to separate a multi-component fluid (e.g., whole blood) into components consistent with an embodiment.

FIG. 1 illustrates one embodiment of a separation system 100, which may be used in, or with, embodiments. In some embodiments, separation system 100 provides for a continuous whole blood separation process. In one embodiment, whole blood is withdrawn from a donor and is substantially, continuously provided to a separation device 104 where the blood is separated into various components and at least one of these components is collected. One or more of the separated components may be either collected for subsequent use or returned to the donor. In embodiments, blood may be withdrawn from the donor and directed through a bag and tubing set 108, which includes a tubing circuit 112, and a fluid processing vessel 116, which together define a closed, sterile and disposable system. The set 108 may be adapted to be mounted in the separation device 104. The separation device 104 includes a pump/valve/sensor assembly 120, which interfaces with the tubing circuit 112, and a centrifuge assembly 124, which interfaces with the fluid processing vessel 116.

Examples of separation systems that may be the basis of systems used with embodiments of the present invention, e.g., separation system 100, include the SPECTRA OPTIA® apheresis system, COBE® spectra apheresis system, and the TRIMA ACCEL® automated blood collection system, all manufactured by Terumo BCT, Inc. of Lakewood, Colo.

The centrifuge assembly 124 may include a channel 128 in a rotatable rotor assembly 132 (e.g., centrifuge), where the channel 128 may be used to hold a fluid processing vessel, e.g., vessel 116. The rotor assembly 132 may rotate to create a centrifugal field. The rotor assembly 132 may be configured to hold a chamber used to separate, concentrate, and/or wash cells. In one example, when whole blood is processed, cellular components of blood may be separated from each other and from liquid components of blood.

The fluid processing vessel 116 may be fitted within the channel 128. In one example, blood can flow substantially continuously from a donor, through the tubing circuit 112, and into the rotating fluid processing vessel 116. Within the fluid processing vessel 116, blood may be separated into various blood component types and at least one of these blood component types (e.g., white blood cells, platelets, plasma, red blood cells, or combinations thereof) may be removed from the fluid processing vessel 116 and further processed. Blood components that are not being retained for collection or for therapeutic treatment (e.g., red blood cells, platelets, white blood cells, and/or plasma) may also be removed from the fluid processing vessel 116 and returned to the donor via the tubing circuit 112.

Operation of the separation device 104 may be controlled by one or more processors included therein, and may comprise a plurality of embedded computer processors that are part of a computer system. The computer system may include a number of components, such as, memory and storage devices (RAM, ROM (e.g., CD-ROM, DVD), magnetic drives, optical drives, flash memory); communication/networking devices (e.g., wired such as modems/network cards, or wireless such as Wi-Fi); input devices such keyboard(s), touch screen(s), camera(s), and/or microphone(s); and output device(s) such as display(s), and audio system(s). The computer system may, in embodiments, control one or more pumps, valves, sensors, etc., such as may be part of assembly 120. In order to interface with an operator of the system 100, embodiments of the separation device 104 may include a graphical user interface 136 (shown in FIG. 1) with a display that includes an interactive touch screen. In embodiments, system 100 may implement one or more features of a computer system, such as computer system 1100 described below with respect to FIG. 11.

Figure 2:
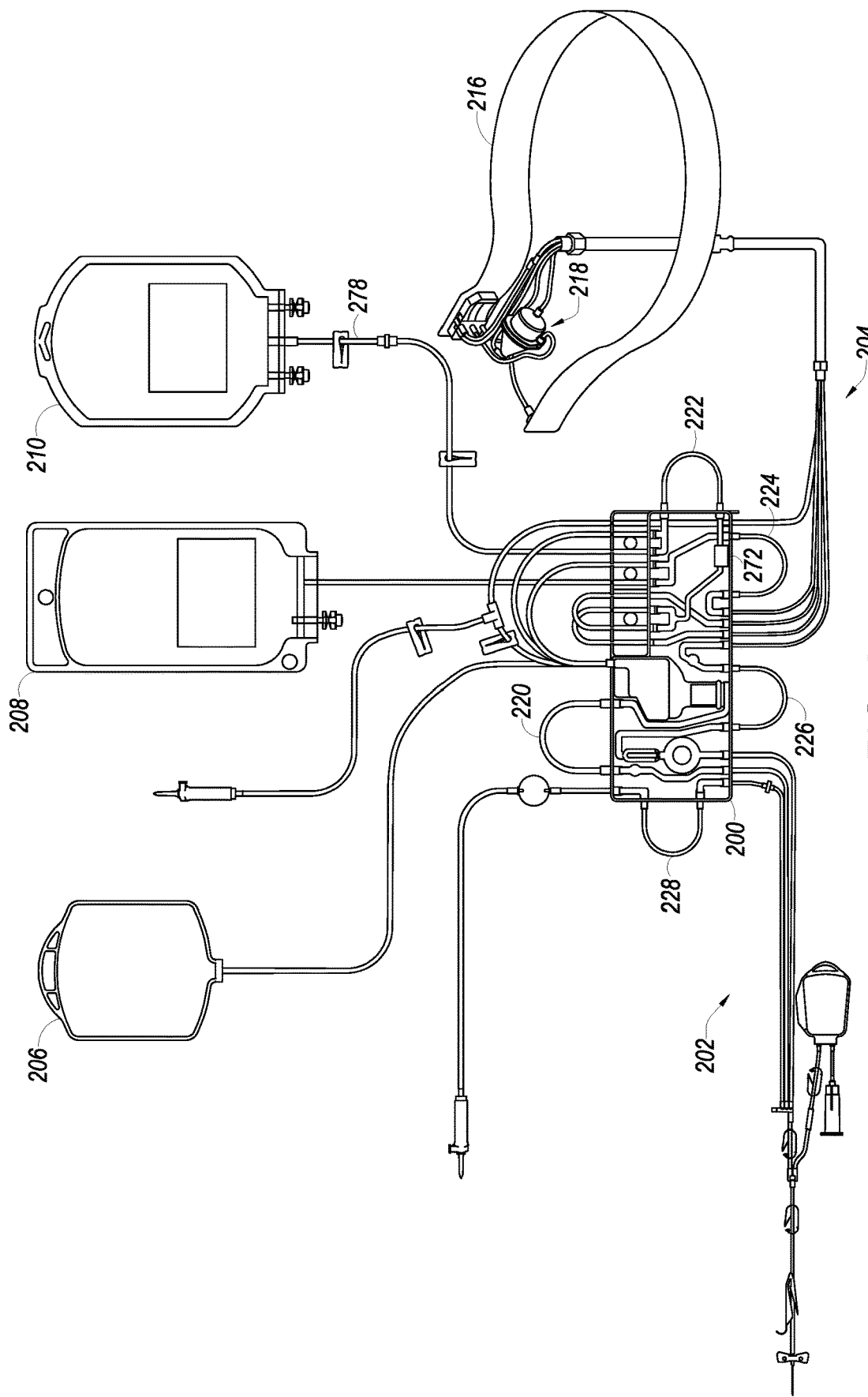
FIG. 2 illustrates a tubing and bag set that may be used in a separation system for separating components of a multi-component fluid (e.g., whole blood) consistent with an embodiment.

An embodiment of a tubing set (e.g., tubing set 108) that may be used with embodiments is shown in FIG. 2. The tubing set may include a cassette 200 and several tubing/storage assemblies 202, 204, 206, 208, and 210. In addition, tubing loops 220, 222, 224, 226, and 228 may engage with peristaltic pumps on a separation device, e.g., device 104 and assembly 120, to pump fluids through the tubing/storage assemblies 202, 204, 206, 208, and 210. The tubing set may also include vessel 216 and chamber 218.

In embodiments, the tubing set shown in FIG. 2 may be used to separate whole blood into components. In embodiments, some components separated from whole blood may be returned to a donor, stored in one or more storage containers, or further processed. For example, whole blood may be circulated through tubing of the tubing set and into the fluid processing vessel 216, which is mounted on a rotor assembly (e.g., assembly 128). Chamber 218 may also be mounted on the rotor assembly.

In the fluid processing vessel 216, the blood may separate into components. Some components may be returned to a donor while others may be further processed. For example, chamber 218 may be used to further process (concentrate or separate) components. In one embodiment, platelets, plasma, and white blood cells may be directed to chamber 218 where they may be further processed (concentrated, separated, etc.) before being stored in a container (e.g., a bag) or returned to a donor. In some of these embodiments, chamber 218 may be designed to concentrate platelets and generate a platelet product with as few white blood cells as possible. In other embodiments, red blood cells separated from whole blood may be introduced into chamber 218 and concentrated before being stored in a container (e.g., a bag). These are merely some examples and embodiments may separate and concentrate other components of whole blood, or other composite fluid.

Figure 3:
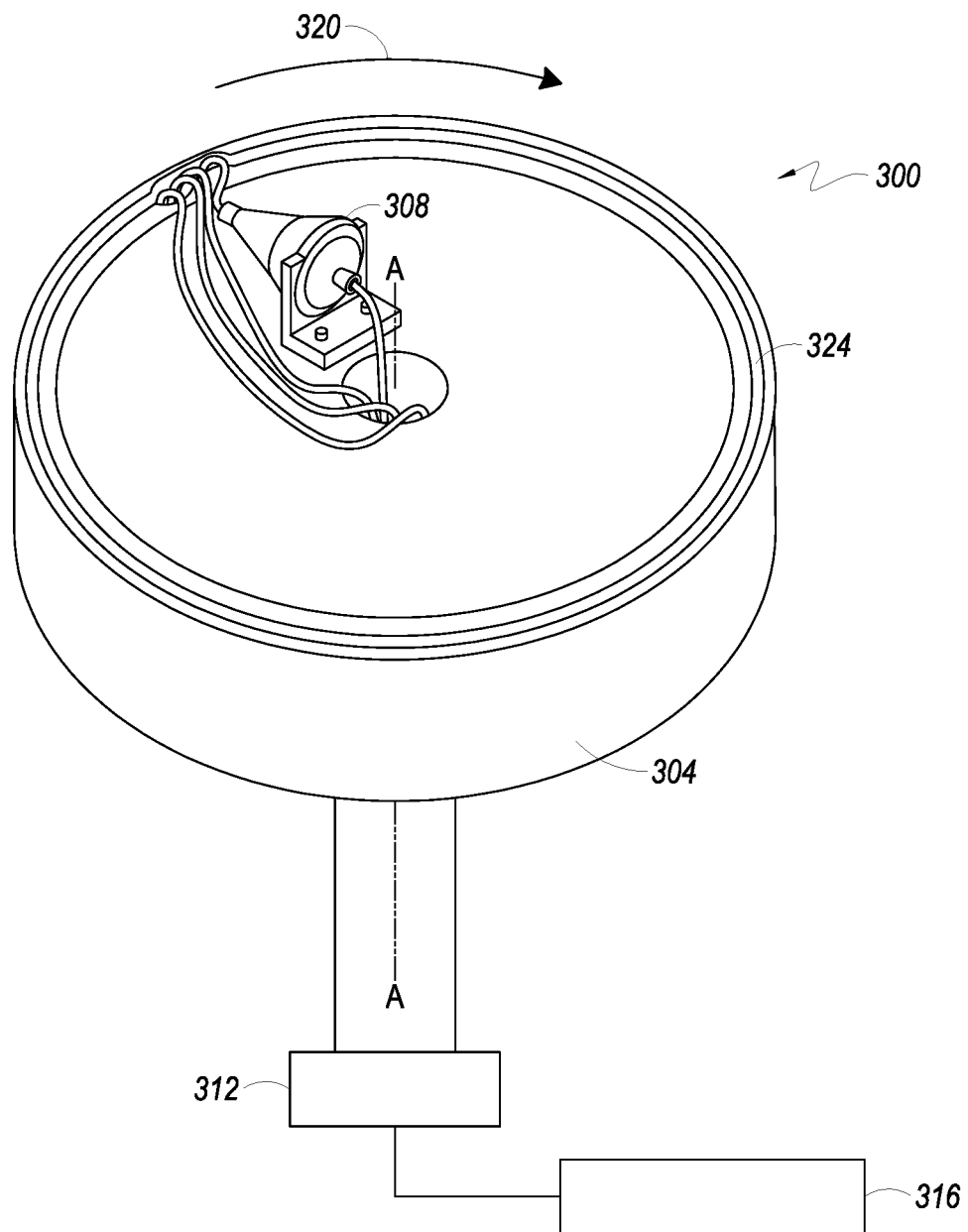
FIG. 3 illustrates a perspective view of a centrifuge and separation chamber that may be used for separating components of a multi-component fluid consistent with embodiments.

FIG. 3 illustrates a perspective view of a portion 300 of a separation system that may be used to separate blood into components as part of a system, such as system 100 (FIG. 1). Portion 300 includes a centrifuge 304, which may be part of a centrifuge assembly (e.g., centrifuge assembly 124 (FIG. 1)). Centrifuge 304 spins around an axis of rotation "A." A separation chamber 308 is also shown, which may be part of a tubing set (e.g., the tubing set shown in FIG. 2). Centrifuge 304 is connected to a motor 312 that spins the centrifuge 304 at very high RPMs. Controller 316 may be connected to motor 312 and be used to control the speed at which motor 312 spins centrifuge 304. Controller 316 may incorporate features of a computer system, such as one or more features of computer system 1100 illustrated in FIG. 11.

In an embodiment, the centrifuge 304 spins in the direction of arrow 320. In other embodiments, centrifuge 304 may spin in an opposite (e.g., counter clockwise) directions. As centrifuge 304 spins, fluid, such as whole blood, within channel 324 may separate into components. In some embodiments, one or more components separated in channel 324 may be further separated in chamber 308. For example, a combination of white blood cells and platelets (e.g., buffy coat) may be further separated within chamber 308.

The spinning of centrifuge 304 around axis A, subjects chamber 308 to a centrifugal field. As described in greater detail below, the centrifugal field may be used to separate the white blood cells and platelets. As may be appreciated, the strength of the centrifugal field may change depending on how fast the centrifuge 304 is spinning. That is, as centrifuge 304 is spun faster, fluid in channel 324 and chamber 308 experience a stronger centrifugal force.

Figure 4:
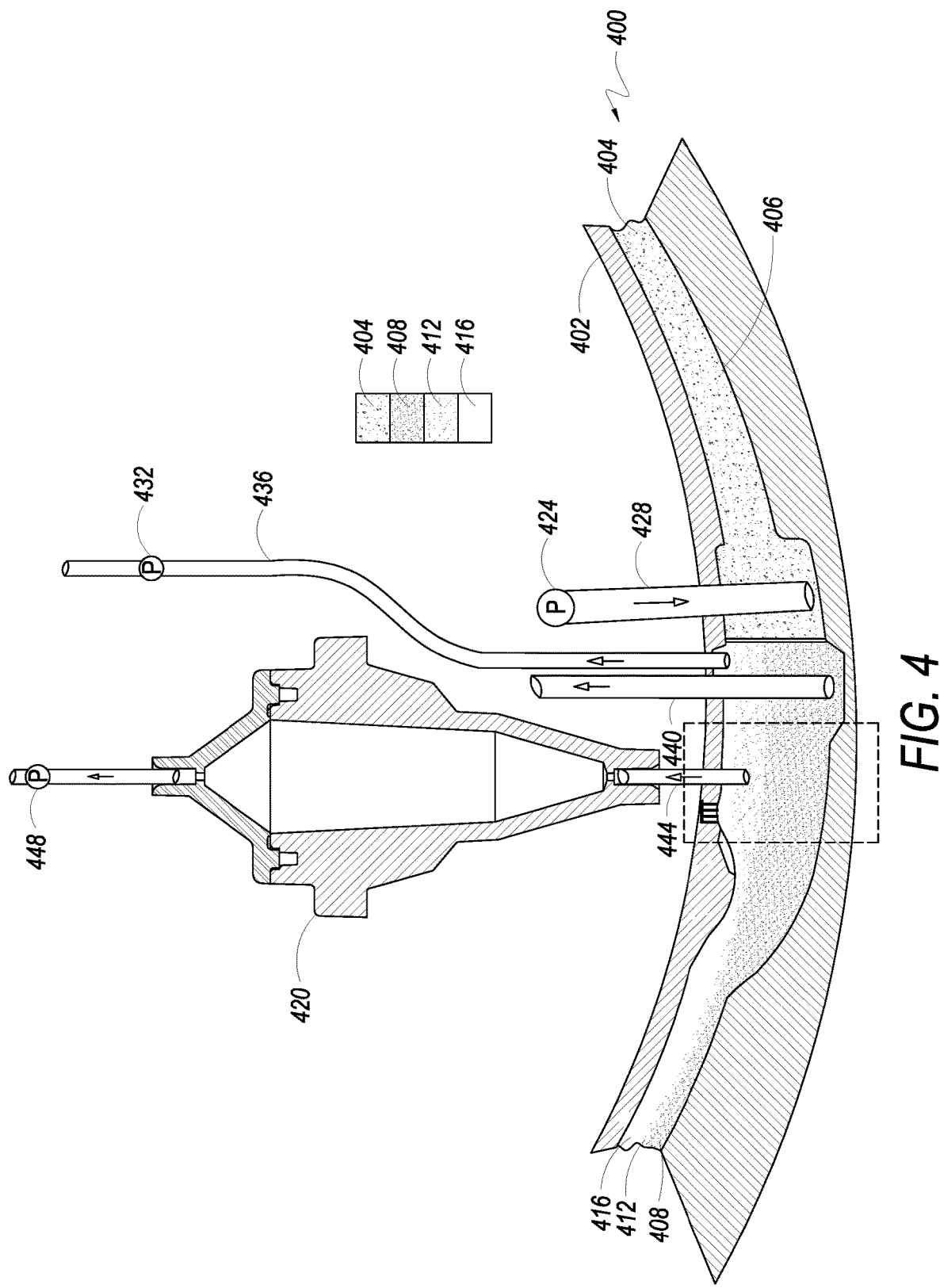
FIG. 4 illustrates a cross-sectional view of a vessel and separation chamber showing the separation of a composite fluid into components.

FIG. 4 illustrates a cross-sectional, partial view, of one embodiment of a centrifuge 400, a vessel 402, and a separation chamber 420 where components are being separated from whole blood, consistent with an embodiment of the present invention. In the embodiment shown in FIG. 4, whole blood 404 is being separated into components that include red blood cells 408, a layer 412 (containing platelets and white blood cells), and plasma 416. The platelets are further separated from the white blood cells in chamber 420.

As shown in FIG. 4, pump 424 pumps whole blood 404 into channel 406 of vessel 402 through conduit 428. Vessel 402 and consequently channel 406, in embodiments, may be positioned around a channel in centrifuge 400, which spins and separates the whole blood 404 into components. On the left side of FIG. 4, whole blood 404 is shown as separated into red blood cells 408, white blood cells/platelets 412, and plasma 416. It is noted that there may also be plasma in the red blood cells and the white blood cells/platelet layers.

Pump 432 removes the separated plasma 416 through conduit 436, which may have an inlet toward a top of channel 406. Conduit 440 may have an inlet toward a bottom of channel 406, which allows red blood cells 408 to be removed from channel 406. Finally, conduit 444 is used to remove white blood cells/platelets 412 from channel 406 and into chamber 420, where the platelets are separated from the white blood cells. In embodiments, as the white blood cells/platelets move into chamber 420, a fluidized bed of particulates may be created, which helps in separating the platelets and white blood cells. A pump 448 may be used to remove concentrated platelets from chamber 420 first, after which separated white blood cells may be removed. Embodiments of methods and systems which may be used to separate platelets from white blood cells are described in greater detail below.

Figure 5:
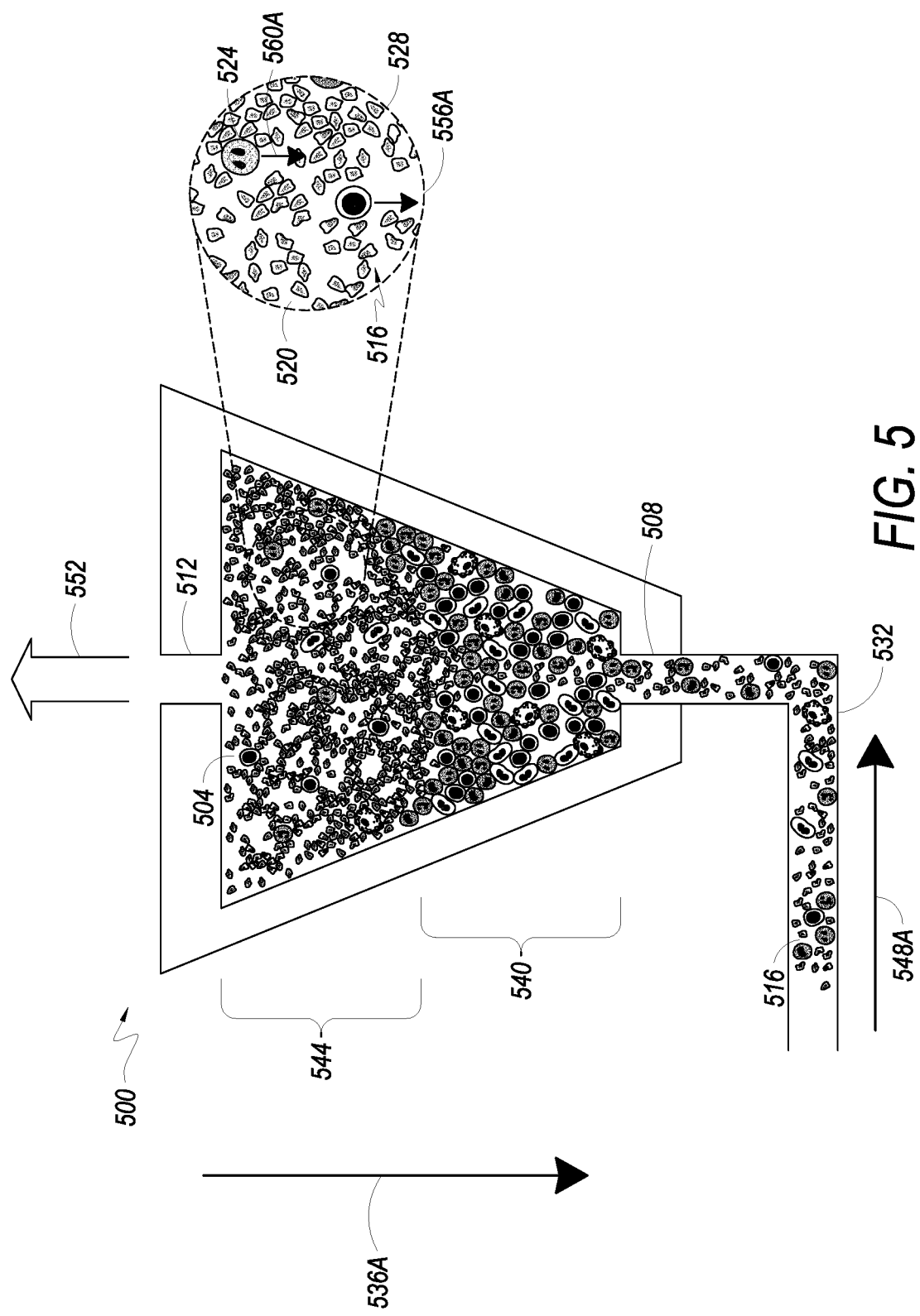
FIG. 5 illustrates a cross-sectional view of a separation chamber separating two particulates consistent with an embodiment.
Figure 6:
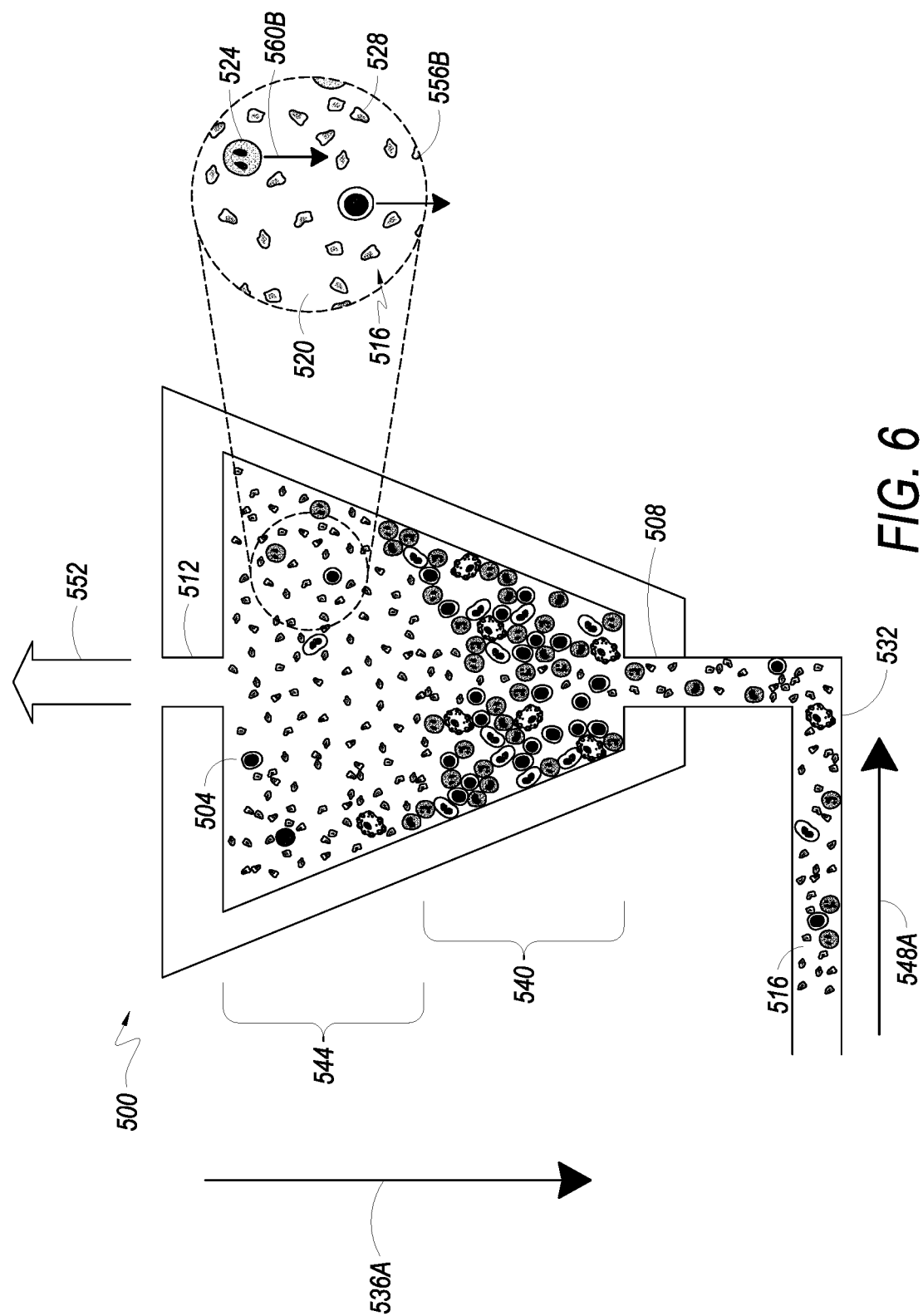
FIG. 6 illustrates a cross-sectional view of a separation chamber separating two particulates consistent with another embodiment.
Figure 7:
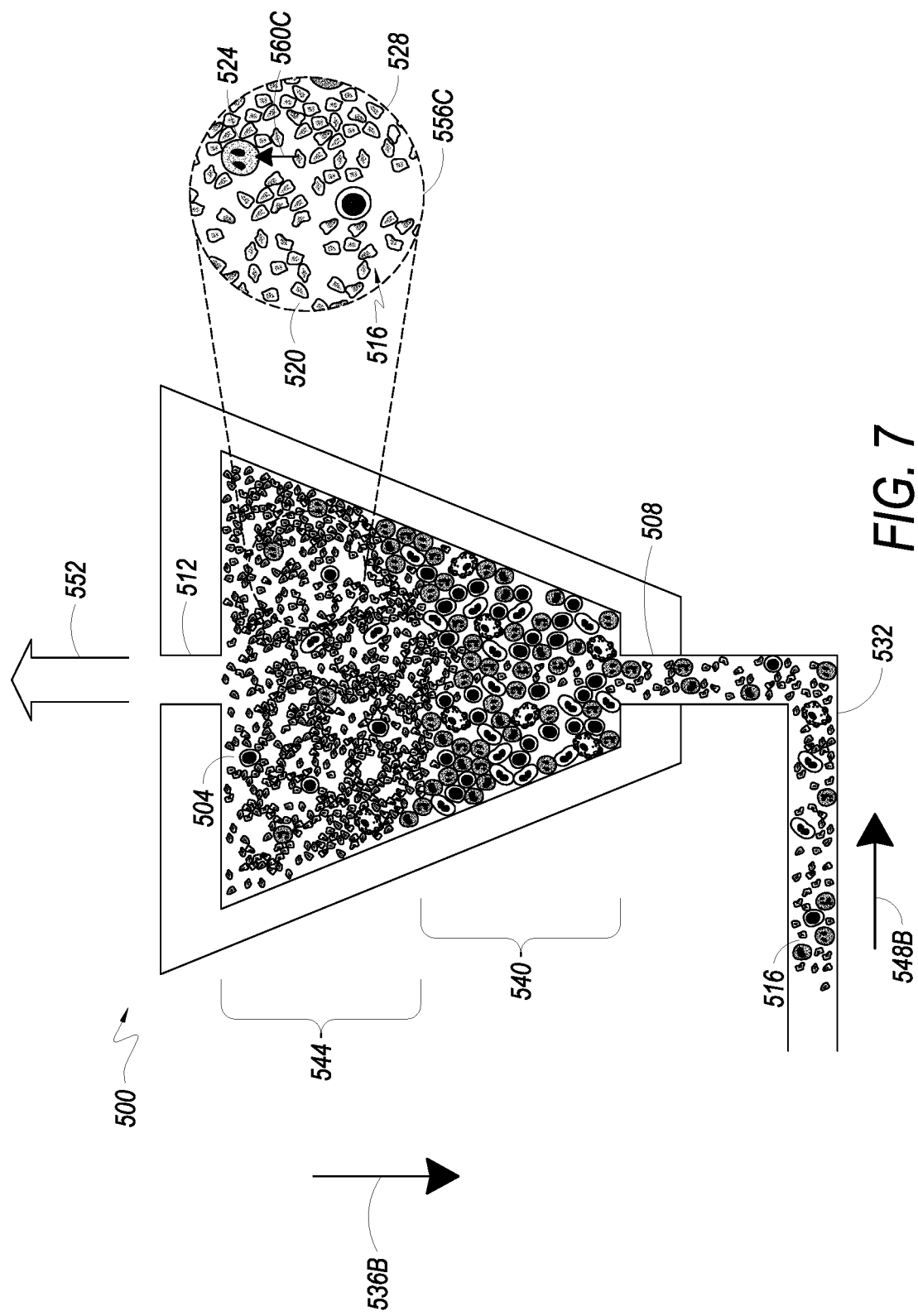
FIG. 7 illustrates a cross-sectional view of a separation chamber separating two particulates consistent with yet another embodiment.

FIG. 5 illustrates a cross-sectional view of a separation chamber 500 separating two particulates consistent with an embodiment. In some embodiments, the separation chamber may be used to separate components of a composite fluid. In the description below FIGS. 5-7 are described with respect to separating platelets from white blood cells, e.g., such as in chambers 218 (FIG. 2), 308 (FIG. 3), and/or 420 (FIG. 4). However, the present invention is not limited thereto. In other embodiments, one or more of the particulates being separated may be other components of blood (e.g., red blood cells, specific types of white blood cells, etc.), components in of other biological fluid(s), and/or components of inorganic fluid (s).

As shown in FIG. 5, separation chamber 500 includes a volume 504, first port 508 and a second port 512. A composite fluid 516, in this embodiment a combination of plasma 520, white blood cells 524, and platelets 528 enters volume 504. A fluid pathway, e.g., tubing 532, is connected to port 508 to allow fluid 516 to enter volume 504. Chamber 500 is subjected to a centrifugal field as illustrated by arrow 536A. Tubing 532 may in embodiments be part of a tubing set (e.g., FIG. 1 and FIG. 2) that may be connected to a vessel (e.g., 116, 216) in which whole blood (or other multi-component fluid) is separated into components, after which the composite fluid 516 with plasma, platelets, and white blood cells may be directed into chamber 500, as described above.

Fluid 516 flows through tubing 532. In embodiments, tubing 532 may be in fluid communication with a separation vessel (e.g., a vessel (402)) where whole blood from a source (e.g., a donor) may be separated into components including a composite fluid 516 that flows from the separation vessel into chamber 500 through tubing 532. At least one pump may control a flow rate of the fluid 516 in tubing 532 into chamber 500 (as illustrated by arrow 548). As fluid flows into volume 504, a fluidized bed of particulates may be created. As the fluid 516 is subjected to the centrifugal field 536, the larger and/or denser particulates, e.g., white blood cells 524 may tend to accumulate in a bottom portion 540 of chamber 500. The lighter particulates (e.g., platelets 528) may tend to move toward a top portion 544 of chamber 500. After a period of time (e.g., when the process reaches a steady state), the less dense platelets 528 may continuously flow out of chamber 500 through port 512, as illustrated by arrow 552. The flow of platelets out of chamber 500 may be collected to generate a platelet in plasma product. In embodiments, a collection bag that may be part of a tubing set may be connected to port 512 to collect the platelets 528.

Without being bound by theory, it is believed that when the density of fluid within volume 504 begins to increase, as a result, e.g., of the accumulation of platelets 528 and white blood cells 524 in volume 504, it may decrease the settling velocity of the white blood cells 524. View 556A illustrates a zoomed-in view of a portion of volume 504 located in the top portion 544 of chamber 500. As illustrated by arrow 560A, the white blood cells 524 have a reduced settling velocity, which may be a result of the high density of the fluid (including the white blood cells and platelets) in top portion 544. This may result in white blood cells 524 remaining in the top portion 544 of chamber 500. Thus, when platelets 528 are removed from chamber 500 to be collected (e.g., in a storage container), they may sweep white blood cells 524 with the platelets in a concentration that is higher than may be desired.

FIG. 6 illustrates another cross-sectional view of separation chamber 500. In the embodiment shown in FIG. 5, a concentration of one or more of the white blood cells 524 and/or platelets 528 has been controlled to ensure that the density of fluid 516 in volume 504 does not reduce the settling velocity of the white blood cells 524 beyond a predetermined amount. Without being bound by theory, it is believed that by maintaining the concentration of one or more of the white blood cells 524 and/or platelets 528 below a predetermined number in the volume 504, the settling velocity can be maintained high enough to ensure that more white blood cells 524 settle into the bottom portion 540 and are not retained in top portion 544 and flow out with the platelets 528.

As shown in FIG. 6, the concentration of white blood cells 524 and/or platelets 528 in fluid 516 are lower than shown in FIG. 5. This may be performed by for example, controlling the amount of fluid pumped from a source of fluid 516. In one embodiment, a pump, which may be drawing whole blood from a donor, e.g., pump 424 (FIG. 4) into a vessel where it is separated to generate plasma, red blood cells, and composite fluid 516 (platelets, plasma, and white blood cells), may have its flow rate reduced so that a smaller volume of whole blood is being separated, which may reduce the white blood cells 524 and/or platelets 528 in fluid 516 flowing into chamber 500. The flow rate 548A through chamber 500 may remain unchanged.

As illustrated in view 556B, which illustrates a zoomed-in view of a portion of volume 504 located in the top portion 544 of chamber 500, the density of the fluid 516 (including the white blood cells and platelets) may be lower, which may allow white blood cells 524 to have a high settling velocity as illustrated by arrow 560B. As a result, fewer white blood cells 524 may remain in the top portion 544 of chamber 500. Accordingly, when platelets 528 flow out of chamber 500 to be collected (e.g., in a storage container), they may contain fewer white blood cells 524.

As illustrated by FIGS. 5 and 6, embodiments may provide for controlling the components flowing into a separation chamber (e.g., separation chamber 500). This may control the density of the fluid in the separation chamber to keep the settling velocity of the white blood cells high enough to allow the white blood cells to settle and not be collected with the platelets.

In embodiments, related to whole blood, the concentration of the platelets (and/or white blood cells), for example, is maintained below a threshold value to ensure that the density of the fluid in the separation chamber does not become too large and reduces the settling velocity of the white blood cells to a point where too many of them escape the separation chamber with the platelets. Initially, a donor's platelet or white blood cell concentration (e.g., count) may be determined. The count may be used to determine how much blood should initially be drawn from a donor, and how that may change (e.g., increase) as the donor is depleted over the course of a procedure.

Some embodiments provide for determining an adjustment based on data regarding an amount of a component (e.g. white blood cells and/or platelets) in a fluid. For example, in one embodiment, a count of a component (e.g., platelet count) may be used to determine how to adjust a draw flow rate of a multi-component fluid introduced into a separation vessel over time.

In operation, chamber 500 may be utilized in a separation process for separating whole blood into components to generate at least a platelet in plasma product. Chamber 500 may be used as separation chamber 420 (FIG. 4), which may be used in a separation system such as system 100 (FIG. 1). System 100 may separate whole blood into plasma, platelets, white blood cells, and red blood cells, with chamber 500 being used to separate the platelets from the white blood cells. In embodiments, when chamber 500 is used in an apheresis separation procedure, the components not being collected may be returned to a donor.

As noted above a donor's platelet or white blood cell concentration (e.g., count) may be determined. This may be done by testing a sample of a donor's blood or alternatively, this may be determined automatically, such as for example using an optical system. The count may be used to determine an adjustment. That is, the count may be used to determine how much blood should initially be drawn from a donor, and how that may change (e.g., increase) as the donor is depleted over the course of a procedure.

A donor may then be connected to system 100 as a whole blood source. Whole blood may be drawn, for example with a pump (e.g., pump 424), from the donor into a separation vessel (e.g., vessel 402) where it is separated into plasma, a composite fluid (platelets/white blood cell fraction), and red blood cells. The platelets/white blood cell fraction may be pumped by a pump (e.g., pump 448) into separation chamber 500.

Initially, the whole blood may be drawn from a donor at a relatively low rate to ensure that the concentration of platelets and/or white blood cells do not increase the density in chamber 500 to a level where white blood cells are swept with the separated platelets. That is, the settling velocity of the white blood cells remains high enough to avoid many white blood cells from remaining in the top portion 544 of the chamber. In embodiments, the density of the fluid in chamber 500 is maintained so that less than about $1 \times 10^6$ white blood cells are collected in a final platelet product for every $3 \times 10^{11}$ platelets in the platelet product collected, e.g., in a storage container.

In embodiments, the amount of blood drawn from the donor may change over time in order to maintain the settling velocity of the white blood cells in chamber 500, but also minimize the time necessary for the procedure. The flow rate of fluid through chamber 500 may remain constant, while the concentration of platelets and white blood cells may change based on the amount of blood drawn from the donor. As one example, when a procedure is performed on a donor with a high platelet count, blood may be drawn from the donor at a lower rate, initially. As the donor is depleted of platelets, the rate of blood drawn from the donor may increase, e.g., proportionally. Increasing the rate of blood drawn from a donor may shorten the procedure, but as noted above, throughout the procedure, the white blood cell settling velocity is maintained to a level that reduces the number of white blood cells swept into the platelets when removed from chamber 500.

FIG. 7 illustrates yet another cross-sectional view of separation chamber 500, according to other embodiments. In FIG. 7, a procedure for collecting a high concentration product of a first component, (e.g., high concentration platelet product) is being performed. In this embodiment, the flow rate through chamber 500 may be less than the flow rates used in FIGS. 5 and 6 as illustrated by arrow 548B.

In embodiments, the flow rate 548B may be determined based on a concentration of a first component in the multi-component fluid, and a desire to collect a concentrated product. In order to achieve a high concentration of the first component, the flow rate 548B may be lower, compared to the process of FIGS. 5 and 6. As a result of the flow rate being lower, the concentration of particles in volume 504 may be higher.

Continuing with the example of platelet products, initially, after a decision is made to perform collection of a concentrated platelet product, and a chamber flow rate is determined, the force of the centrifugal field illustrated by arrow 536 may be determined. In embodiments, the force of the centrifugal field may be controlled by the speed at which the centrifuge (on which chamber 500 is mounted) is rotated. The speed may, in embodiments, be determined based on collection of a concentrated platelet product and the chamber flow rate determined based on the concentration of the first component in the composite.

Without being bound by theory, it is believed that when collecting a concentrated product and selecting a chamber flow rate based on a concentration of a first component in a multi-component fluid (e.g., platelet or white blood cell count), a lower chamber flow rate may result in a higher concentration of components in the chamber. In order to offset the higher concentration of components, the centrifugal force 536B may be lower so that fewer of the other components are swept into the concentrated product. The lower centrifugal force (generated by a lower centrifuge speed) may allow platelets to move toward the top portion 544 as shown by arrow 560C. Compared to conventional processes, which may provide for using the same predetermined centrifuge speed for all processes of collecting a concentrated product (regardless of chamber flow rates), embodiments that provide for selecting the centrifuge speed based on the chamber flow rates may generate a concentrated product with fewer of other particulates.

In embodiments, a concentrated platelet product may be generated with less than about $1 \times 10^6$ white blood cells being collected in a final product of concentrated platelets for every $3 \times 10^{11}$ of the platelets.

FIGS. 5-7 are provided merely for illustrative purposes. Other embodiments, may provide for separating other particulates (of different sizes and/or density) from composite fluids other than blood. For example, embodiments may provide for separating inorganic particulates of different sizes, weights, densities, etc. Also, embodiments may provide for separating other components from blood. For example, embodiments may separate white blood cells from red blood cells. In other embodiments, different types of white blood cells may be separated. Accordingly, the present invention is not limited to the specific embodiments described above with respect to FIGS. 5-7.

Further, although chamber 500 is shown with a design, embodiments may provide for other designs. As shown above, chamber 500 may have a conical shaped volume. In other embodiments, chamber 500 may have a volume of a different shape, including without limitation, cube, sphere, ellipsoid, tear shaped, rectangular prism, etc.

In embodiments, chamber 500 may include other features that may help in the separation of particles. In some embodiments, chamber 500 may be referred to as an LRS chamber and include one or more features described in any one of U.S. Pat. Nos. 5,674,173; 6,053,856; 6,334,842; and 7,963,901; all of which are hereby incorporated by reference in their entirety as if set forth herein in full. For example, in embodiments, chamber 500 may have grooved or stepped features on an inside surface as shown and described in U.S. Pat. No. 5,674,173. These are merely some examples, and the present invention is not limited thereto.

Figure 8:
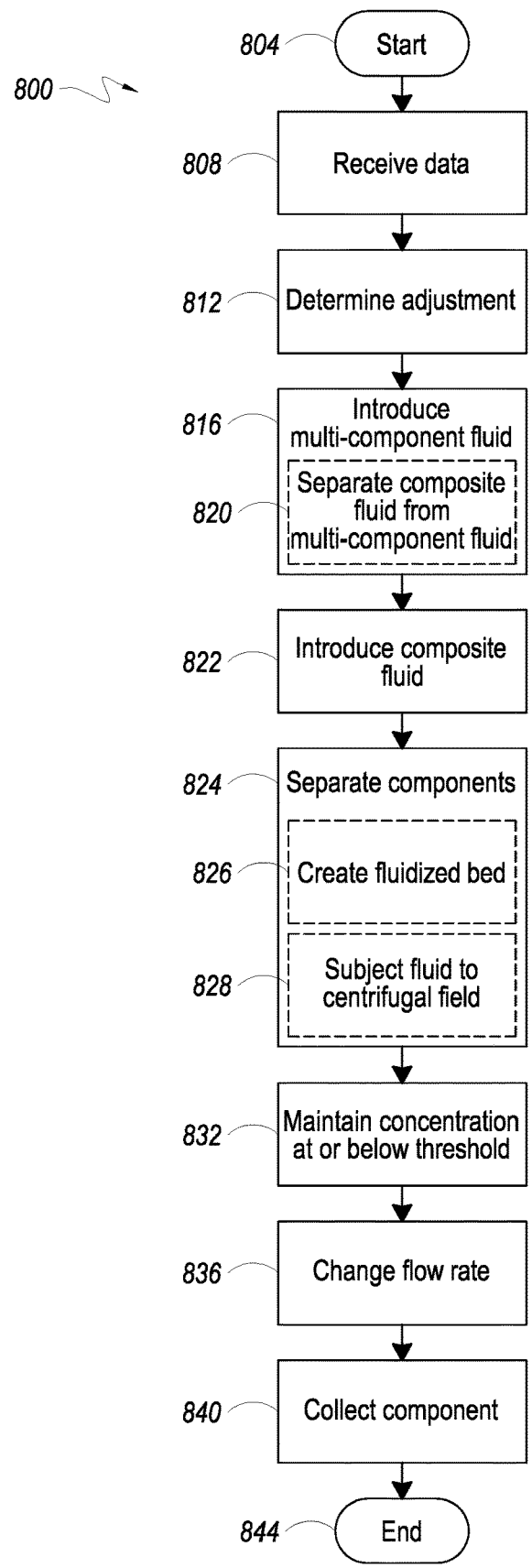
FIG. 8 illustrates a flow diagram of a process for collecting a component from a composite fluid consistent with an embodiment.
Figure 9:
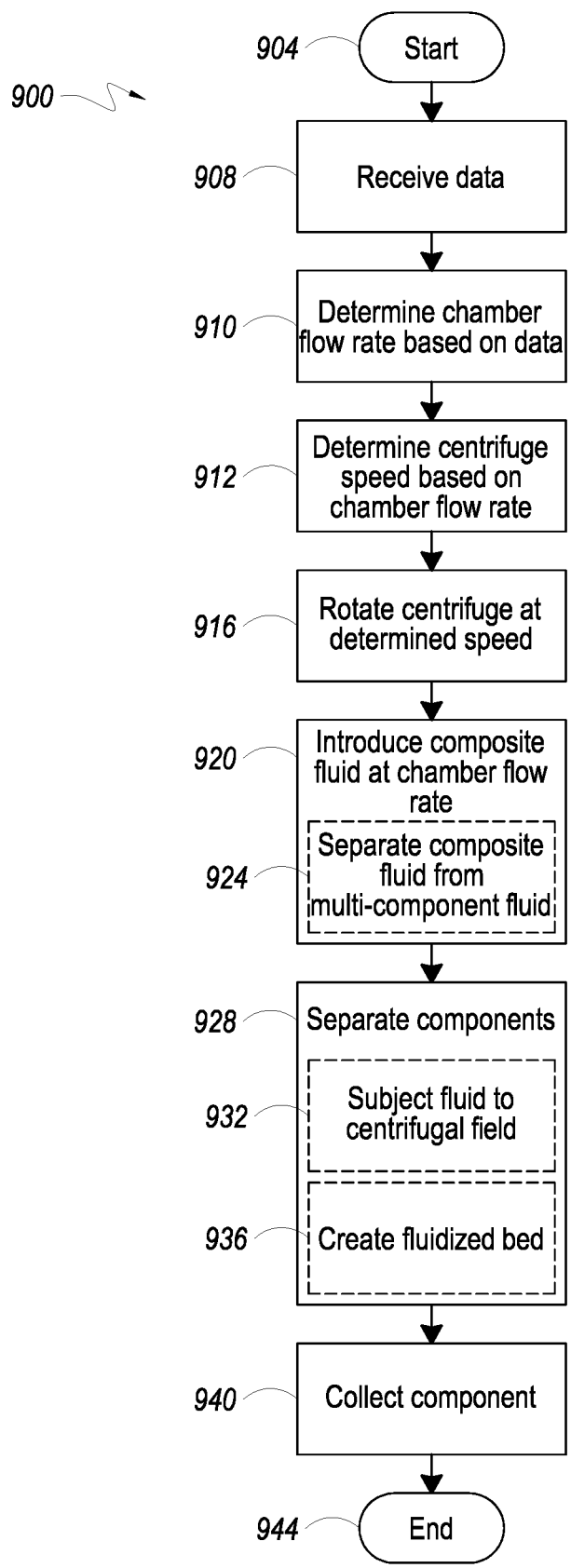
FIG. 9 illustrates a flow diagram of a process for collecting a component from a composite fluid consistent with another embodiment.
Figure 10:
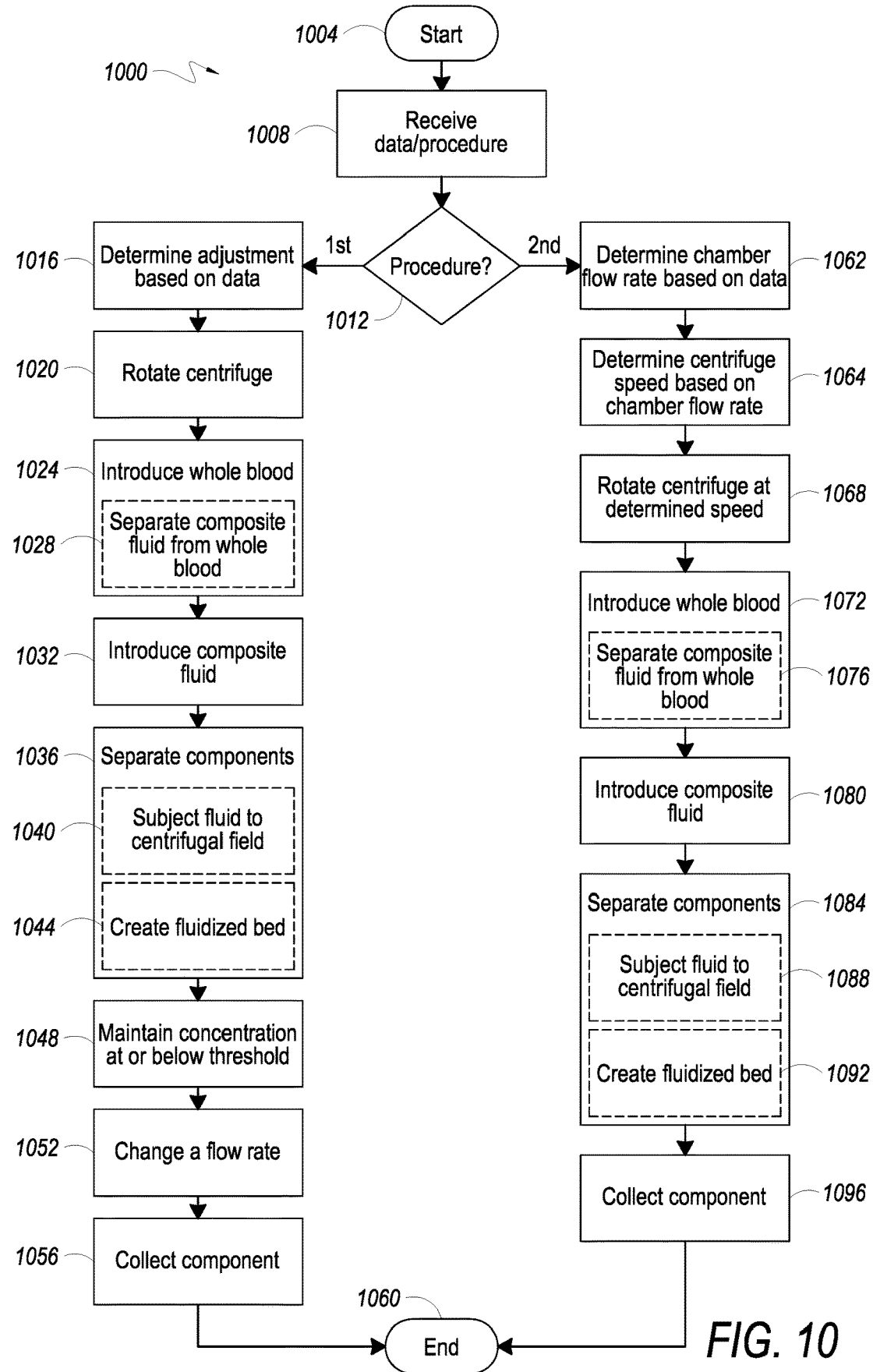
FIG. 10 illustrates a flow diagram of processes for collecting a component from whole blood consistent with yet another embodiment.

FIGS. 8, 9, and 10 illustrate flow charts 800, 900, and 1000 that may be performed in embodiments of the present invention. Although specific devices may be described below for performing steps in flow charts 800, 900, and 1000, the present invention is not limited thereto. For example, some steps may be described as performed by a processor, e.g., processor 1112 (FIG. 11) or a chamber, e.g., chamber 500 (FIGS. 5-7). This is done merely for illustrative purposes, and flow charts 800, 900, and 1000 are not limited to being performed by any specific device.

Flow chart 800 illustrates processes consistent with embodiments of the present invention for separating/collecting component(s) from a composite fluid separated from a multi-component fluid. In embodiments, flow chart 800 may be implemented by a separation system such as system 100 (FIG. 1) to separate component(s) from whole blood. For example, flow chart 800 may be used to separate/collect a platelet component that is separated from whole blood. However, flow chart 800 is not limited to separating/collecting component(s) of whole blood and in embodiments may be used to separate/collect different types of particulates.

Flow chart 800 starts at 804. Flow passes from 804 to optional step 808, where first data may be received. The first data may indicate concentration of components in the multi-component fluid. In embodiments, step 808 may involve some sub-steps. For example, in one embodiment, an operator may input a concentration into a user interface (UI) (e.g., user interface 136). As one example, if the multi-component fluid that will be separated into components is whole blood, the data input at step 808 may be a concentration of a blood component. The concentration may be determined by an operator performing tests or some analysis on samples of the whole blood to determine a concentration. In one embodiment involving whole blood, the data may be a concentration (e.g., a count) of platelets or white blood cells in whole blood.

In other embodiments, the data received at step 808 may be received from an imaging system. For example, the data may be image data taken by one or more cameras. In other embodiments, the data may be received from a light detector that detects light transmitted or reflected by the multi-component fluid and/or the separated components. The reflected or transmitted light may be used to calculate a concentration such as a platelet or white blood cell count. In embodiments, a processor, such as processor 1112 (FIG. 11) that may be part of a separation apparatus (e.g., apparatus 104) may receive the data at step 808.

After step 808, flow passes to step 812, where, based on the data received at step 808, a determination regarding an adjustment is made. In embodiments, a processor, e.g., processor 1112 (FIG. 11) may make the determination. Depending on a particular procedure being performed, an adjustment may relate to how fast to draw the multi-component fluid from a source, initially, and how the rate may be adjusted, e.g., higher, as the procedure proceeds. Therefore, the adjustment determined at step 812 may relate to: a parameter that results in changes in fluid flow (e.g., flow rates of fluid drawn from a source). In embodiments, a processor, such as processor 1112 (FIG. 11) that may be part of a separation apparatus (e.g., apparatus 104) may make the determination of the adjustment at step 812.

After step 812, step 816 may be performed to introduce a multi-component fluid into a separation vessel at a predetermined rate. As part of step 816, a composite fluid may be separated from the multi-component fluid at optional step 820. As one example, noted above, whole blood may be separated into components in a separation vessel, e.g., vessel 402. Whole blood may be separated into plasma, platelets/white blood cells, and red blood cells. The composite fluid separated at step 820, may in embodiments include platelets with white blood cells that were initially separated from whole blood in the separation vessel. In other embodiments, the composite fluid may include white blood cells and red blood cells.

Flow 800 then passes to 822 where the composite fluid, separated from the multi-component fluid at step 820, may be introduced into a separation chamber. The separation chamber in embodiments may be designed to separate particulates of at least two different types. The flow rate of the composite fluid through the chamber may remain constant throughout the procedure. In embodiments, the fluid introduced into the separation chamber may include one or more components of whole blood, e.g., plasma, platelets, white blood cells, and/or red blood cells.

From step 822, flow 800 proceeds to step 824 where components of the composite fluid are separated. In embodiments, step 824 may involve one or more sub-steps. For example, in one embodiment, a fluidized bed may be generated at optional step 826. Examples of fluidized beds are shown in FIGS. 5-7. Optional step 826 may involve any number of steps or structures, for example, the separation chamber may have a design for creating the fluidized bed (e.g., conical shaped volume, stepped sides, etc.). In some embodiments, fluid may be introduced at positions into a separation chamber, at particular flow rates, etc. to aid in establishing the fluidized bed.

As part of step 824, the fluid may be subjected to a centrifugal field. Step 824 may therefore involve sub-step 828, where the fluid is subjected to a centrifugal field. The centrifugal field may be established by for example having the separator on a system with a centrifuge assembly that rotates. As one example, the separation chamber may be mounted on a centrifuge assembly as shown above with respect to FIGS. 1 and 3. The centrifuge may rotate as fluid flows through the separation chamber, subjecting the fluid to the centrifugal field. In embodiments, the centrifuge may be spun by a motor, e.g., motor 312 (FIG. 3), and be controlled by a computer system, e.g., controller 316 (FIG. 3).

After step 824, flow 800 passes to step 832, where the concentration of a component may be maintained at or below a threshold value. As described above with respect to FIGS. 5 and 6, flow 800 may be used for a process of collecting, for example, platelets in plasma. In order to collect the platelets with as few white blood cells as possible, the density of the fluid in the separation chamber may be maintained below a predetermined density. As noted above with respect to FIGS. 5 and 6, the density may affect the settling velocity of components (e.g., white blood cells). To maintain the particular density, the concentration of platelets in a separation chamber, for example, are maintained at or below a threshold amount in step 832. In embodiments, to accomplish this, a pump, drawing whole blood from a source and into a separation vessel (e.g., step 816), could be initially slowed down to control the amount of platelets flowing into the separation chamber.

Step 836 may be performed to change a flow rate of a fluid during the process of flow 800. Continuing with the example above (with respect to step 832) the concentration of platelets in a source (e.g. donor) may initially be high. As a result, flow 800 may provide for having a lower flow rate of fluid drawn from a donor and into a vessel, initially (e.g., step 816). That is, the flow rate introduced into the separation vessel at 816, may be at a first predetermined rate. After a predetermined period of time, the donor may have their platelets depleted. At that point, step 836 may provide for changing the flow rate (e.g. to a second rate) of the pump that is drawing fluid from the donor and being introduced into the separation vessel. For example, the pump flow rate may be increased to draw more whole blood for separating since the depleted platelet level would not bring the concentration in the separation chamber above the threshold. Step 840 may also utilize the adjustment determined at step 812. That is, based on the adjustment determined at step 812, a pump introducing multi-component fluid into a separation vessel may be increased by a particular amount, after a predetermined period of time from the point where the procedure started. The changes in the flow rate may be effected by a processor (e.g., 1112) that may be used to control a draw flow pump, e.g., pump 424 (FIG. 4).

Flow 800 then passes to step 844 where a component, e.g., platelets, is collected. Step 844 may involve, in embodiments, moving the components from the separation chamber to a storage container for collection. In embodiments, the component may be collected in a soft storage container such as a bag that may be part of a tubing set, e.g., as shown in FIG. 2. Flow 800 then ends at 844.

Flow chart 900 illustrates processes consistent with embodiments of the present invention for separating/collecting component(s) from a composite fluid. In embodiments, flow chart 900 may be implemented by a separation system such as system 100 (FIG. 1) to separate component(s) from whole blood. For example, flow chart 900 may be used to separate/collect a concentrated platelet component that is separated from whole blood. However, flow chart 900 is not limited to separating/collecting component(s) of whole blood and in embodiments may be used to separate/collect different types of particulates.

Flow chart 900 starts at 904. Flow passes from 904 to step 908, where data may be received. The data may indicate concentration of one or more components in a multi-component fluid, such as whole blood. In embodiments, step 908 may involve some sub-steps. For example, in one embodiment, an operator may input a concentration into a user interface (UI) (e.g., user interface 136). As one example, if the multi-component fluid that will be separated into components is whole blood, the data input at step 908 may be a concentration of a blood component. The concentration may be determined by an operator performing tests or some analysis on samples of the whole blood to determine a concentration. In one embodiment involving whole blood, the data may be a concentration (e.g., a count) of platelets and/or white blood cells.

In other embodiments, the data received at step 908 may be received from an imaging system. For example, the data may be image data taken by one or more cameras. In other embodiments, the data may be received from a light detector that detects light transmitted or reflected by the multi-component fluid and/or the separated components. The reflected or transmitted light may be used to calculate a concentration such as a platelet or white blood cell count. In embodiments, a processor, such as processor 1112 (FIG. 11) that may be part of a separation apparatus (e.g., apparatus 104) may receive the data at step 908.

After step 908, flow passes to step 910, where, based on the data received at step 908, a determination of a chamber flow rate for the procedure is made. In embodiments, a processor, e.g., processor 1112 (FIG. 11) may make the determination. In some embodiments, the determination is made based, at least in part, on the data received at step 908. For example, as noted above, the data received at step 908 may relate to a concentration of a component in the multi-component fluid. In one embodiment, if the concentration of a component in the multi-component fluid is low, the chamber flow rate may be lower than if the concentration of the component in the multi-component fluid is higher. In other words, the chamber flow rate may change between procedures based on the concentration of components in the multi-component liquid being separated. These are merely some examples and the present invention is not limited thereto.

After step 910, flow passes to step 912, where, based on the chamber flow rate determined at step 910, a determination of a centrifuge speed for the procedure is made. In embodiments, a processor, e.g., processor 1112 (FIG. 11) may make the determination. In some embodiments, the determination is made based, at least in part, on the chamber flow rate, which as described above is determined at least in part by the data received at step 908. In other words, the centrifuge speed may change between procedures based on the chamber flow rate determined at step 910.

Flow 900 then passes to step 916, where the centrifuge (e.g., 124 or 304), is rotated at the speed determined at step 912. After step 916, flow passes to 920 where a composite fluid may be introduced into a separation chamber at the chamber flow rate determined at step 910. The separation chamber in embodiments may be designed to separate particulates of at least two different types. In some embodiments, the fluid introduced into the separation chamber may be components of whole blood.

It is noted that in some embodiments, the fluid introduced at step 920 may have previously been separated from a multi-component fluid. Optional step 924 may be performed to separate the composite fluid from a multi-component fluid. As one example, noted above, whole blood may be separated into components in a separation vessel, e.g., vessel 402. Whole blood may be separated into plasma, platelets/white blood cells, and red blood cells. The composite fluid introduced into the separation chamber at step 920 may, in embodiments, include platelets with white blood cells that were initially separated from whole blood in a separation vessel.

From step 920, flow 900 proceeds to step 928 where components of the composite fluid are separated. In embodiments, step 928 may involve one or more sub-steps. As part of step 928, the fluid may be subjected to a centrifugal field created by the rotation of the centrifuge at step 916. Step 928 may therefore involve sub-step 932, where the fluid is subjected to a centrifugal field. The centrifuge may spin as fluid flows through the separation chamber, subjecting the fluid to the centrifugal field. In embodiments, the centrifuge may be spun by a motor, e.g., motor 312 (FIG. 3), and be controlled by a computer system, e.g., controller 316 (FIG. 3).

In addition, a fluidized bed may be generated at optional step 936. Examples of fluidized beds are shown in FIGS. 5-7. Optional step 936 may utilize structures, for example, the separation chamber may have a specific design for creating the fluidized bed, e.g., conical shaped volume, stepped sides, etc. In some embodiments, fluid may be introduced at a particular location in a separation chamber, at particular flow rates, etc. to aid in establishing the fluidized bed.

Flow 900 then passes to step 940 where a component, e.g., platelets, is collected. Step 940 may involve, in embodiments, moving the components from the separation chamber to a storage container for collection. In embodiments, the component may be collected in a soft storage container such as a bag that may be part of a tubing set, e.g., as shown in FIG. 2. Flow 900 then ends at 944.

Flow chart 1000 illustrates processes that combine aspects of flows 800 and 900 consistent with embodiments of the present invention for separating/collecting component(s) from a composite fluid separated from whole blood. In embodiments, flow chart 1000 may be implemented by a separation system such as system 100 (FIG. 1), which performs apheresis procedures for collecting a product that includes components of whole blood. The product may in embodiments be a standard platelet in plasma product, (e.g. about 1500×10³ platelets per microliter) or a concentrated platelet in plasma product (e.g. about 4000×10³ platelets per microliter). Other products may also be collected in other embodiments and may include other components of whole blood, such as red blood cells and/or white blood cells.

Flow chart 1000 starts at 1004. Flow passes from 1004 to step 1008, where data as well as an indication about a procedure may be received. As described in greater detail below, the procedure may be a first procedure for collecting a product including a component of whole blood, or a second procedure for collecting a concentrated product including a more concentrated amount of the component of whole blood. In addition, the data received at step 1008 may relate to a concentration of the component in the whole blood. For example, the data may in embodiments relate to a platelet or a white blood cell count. In embodiments, step 1008 may involve some sub-steps. For example, in one embodiment, an operator may input the procedure and/or data into a user interface (UI) (e.g., user interface 136).

In some embodiments, the data received at step 1008 may be received from an imaging system. For example, the data may be image data taken by one or more cameras. In other embodiments, the data may be received from a light detector that detects light transmitted or reflected by the whole blood and/or the separated components. The reflected or transmitted light may be used to calculate a concentration such as a platelet or white blood cell count. In embodiments, a processor, such as processor 1112 (FIG. 11) that may be part of a separation apparatus (e.g., apparatus 104) may receive the data at step 1008.

After step 1008, flow passes to decision 1012, where it is determined what procedure was received at step 1008. In embodiments, a processor, e.g., processor 1112 (FIG. 11) may make the determination. If at decision 1012 it is determined that a first procedure was indicated, flow passes to step 1016. In embodiments, the first procedure may be for collecting a product with a standard concentration of platelets in plasma.

At step 1016, a determination regarding an adjustment is made based on the data received at step 1008. In embodiments, a processor, e.g., processor 1112 (FIG. 11) may make the determination. The adjustment may relate to how fast to draw whole blood from a donor, initially, and how the rate may be adjusted, e.g., higher or lower, as the procedure proceeds.

After step 1016, step 1020 may be performed to rotate a centrifuge. In embodiments, the centrifuge may be rotated at a first predetermined speed. The first predetermined speed may, in embodiments, be the same for any procedure performed to generate a product with a standard concentration of platelets in plasma.

After step 1020, whole blood may be introduced into a separation vessel at a first predetermined rate at step 1024. As part of step 1024, a composite fluid may be separated from the whole blood at optional step 1028. The whole blood may be separated into components in the separation vessel, e.g., vessel 402. Whole blood may be separated into plasma, platelets/white blood cells (e.g., a composite fluid), and red blood cells.

Flow 1000 then passes to step 1032 where the composite fluid separated at step 1028 (e.g., platelets/white blood cells) is introduced into a separation chamber. At step 1036, the composite fluid is separated in the separation chamber into a first component and a second component.

In embodiments, step 1036 may involve one or more sub-steps. As part of step 1036, the fluid may be subjected to a centrifugal field created by the rotation of the centrifuge at step 1020. The centrifuge may spin as fluid flows through the separation chamber, subjecting the fluid to the centrifugal field. In embodiments, the centrifuge may be spun by a motor, e.g., motor 312 (FIG. 3), and be controlled by a computer system, e.g., controller 316 (FIG. 3).

In addition, a fluidized bed may be generated at optional step 1044. Examples of fluidized beds are shown in FIGS.

5-7. Optional step 1044 may utilize structures, for example, the separation chamber may have a specific design for creating the fluidized bed, e.g., conical shaped volume, stepped sides, etc. In some embodiments, fluid may be introduced at a particular location in the separation chamber, at particular flow rates, etc. to aid in establishing the fluidized bed.

Flow 1000 may then pass to step 1048, where the concentration of a component may be maintained at or below a threshold value. In the case of platelet collection, in order to collect the platelets with as few white blood cells as possible, the density of the fluid in the separation chamber may have to be maintained below a predetermined density as described. As noted above with respect to FIGS. 5 and 6, the density may affect the settling velocity of components (e.g., white blood cells). To maintain the density at an appropriate level, the concentration of platelets in the separation chamber, for example, are maintained at or below a threshold amount at step 1048. In embodiments, to accomplish this, a pump, drawing blood from a donor into the separation vessel at step 1024 may be initially slow to control the amount of platelets flowing into the separation chamber.

After step 1048, step 1052 may be performed to change a flow rate of whole blood introduced at step 1024. Continuing with the example above (with respect to step 1048) the concentration of platelets in a donor may initially be high. As a result, flow 1000 may provide for having a lower flow rate of whole blood drawn from a donor and into a vessel, initially. That is, the flow rate introduced into the separation vessel at 1024, may be at a first predetermined rate. After a predetermined period of time, the donor may have their platelets depleted. At that point, step 1052 may provide for changing the flow rate of the pump (e.g., a second flow rate) that is drawing fluid from the donor and being introduced into the separation vessel. For example, the pump flow rate may be increased to draw more whole blood for separating since the depleted platelet level would not bring the concentration in the separation chamber above the threshold. Step 1052 may utilize the adjustment determined at step 1016. That is, based on the adjustment determined at step 1016, a pump introducing whole blood into the separation vessel may be increased by a particular amount, after a predetermined period of time from the point where the procedure started. The changes in the flow rate may be effected by a processor (e.g., 1112) that may be used to control a draw flow pump, e.g., pump 424 (FIG. 4).

Flow 1000 then passes to step 1056 where a component, e.g., platelets, is collected. In embodiments, the component may be collected in a soft storage container such as a bag that may be part of a tubing set, e.g., as shown in FIG. 2. Flow 1000 then ends at 1060.

Referring back to decision 1012, if a decision is made that the procedure is a second procedure, flow 1000 passes to step 1062. At step 1062, a determination of a chamber flow rate for the procedure is made. In embodiments, a processor, e.g., processor may make the determination. In some embodiments, the determination is made based, at least in part, on the data received at step 1008. For example, as noted above, the data received at step 1008 may relate to a concentration (e.g., platelet count, white blood cell count, etc.) of a component in whole blood. In one embodiment, if the concentration of a component in the whole blood is low, the flow rate may be lower than if the concentration of the component in the whole blood is higher. In other words, the chamber flow rate may change between procedures based on the concentration of components in the whole blood being separated. These are merely some examples and the present invention is not limited thereto.

At step 1064, a centrifuge speed for the procedure is determined. In embodiments, a processor may make the determination. In some embodiments, the determination is made based, at least in part, on chamber flow rate determined at step 1062. In one embodiment, if the chamber flow rate is relatively low, the speed of the centrifuge may be lower than if the chamber flow rate is higher.

Flow 1000 then passes to step 1068, where the centrifuge (e.g., 124 or 304), is rotated at the speed determined at step 1064. After step 1068, flow 1000 passes to step 1072, where whole blood may be introduced into a separation vessel. As part of step 1072, a composite fluid may be separated from the whole blood at optional step 1076. The whole blood may be separated into components in the separation vessel, e.g., vessel 402. Whole blood may be separated into plasma, platelets/white blood cells (e.g., a composite fluid), and red blood cells.

Flow 1000 then passes to step 1080 where the composite fluid separated at step 1076 (e.g., platelets/white blood cells) is introduced into a separation chamber at the flow rate determined at step 1062. At step 1084, the composite fluid is separated in the separation chamber into a first component and a second component.

In embodiments, step 1084 may involve one or more sub-steps. As part of step 1084, the fluid may be subjected to a centrifugal field created by the rotation of the centrifuge at step 1088. The centrifuge may spin as fluid flows through the separation chamber, subjecting the fluid to the centrifugal field. In embodiments, the centrifuge may be spun by a motor, e.g., motor 312 (FIG. 3), and be controlled by a computer system, e.g., controller 316 (FIG. 3).

In addition, a fluidized bed may be generated at optional step 1092. Examples of fluidized beds are shown in FIGS. 5-7. Optional step 1092 may utilize structures, for example, the separation chamber may have a specific design for creating the fluidized bed, e.g., conical shaped volume, stepped sides, etc. In some embodiments, fluid may be introduced at a location in the separation chamber, at particular flow rates, etc. to aid in establishing the fluidized bed.

Flow 1000 then passes to step 1096 where a component, e.g., platelets, is collected. In embodiments, the component may be collected in a soft storage container such as a bag that may be part of a tubing set, e.g., as shown in FIG. 2. Flow 1000 then ends at 1060.

Although flows 800, 900, and 1000 have been described with steps listed in a particular order, the present invention is not limited thereto. In other embodiments, steps may be performed in different order, in parallel, or any different number of times, e.g., before and after another step. Also, as indicated above, flows 800, 900, and 1000 may include some optional steps/sub-steps. However, those steps above that are not indicated as optional should not be considered as essential to the invention, but may be performed in some embodiments of the present invention and not in others.

Figure 11:
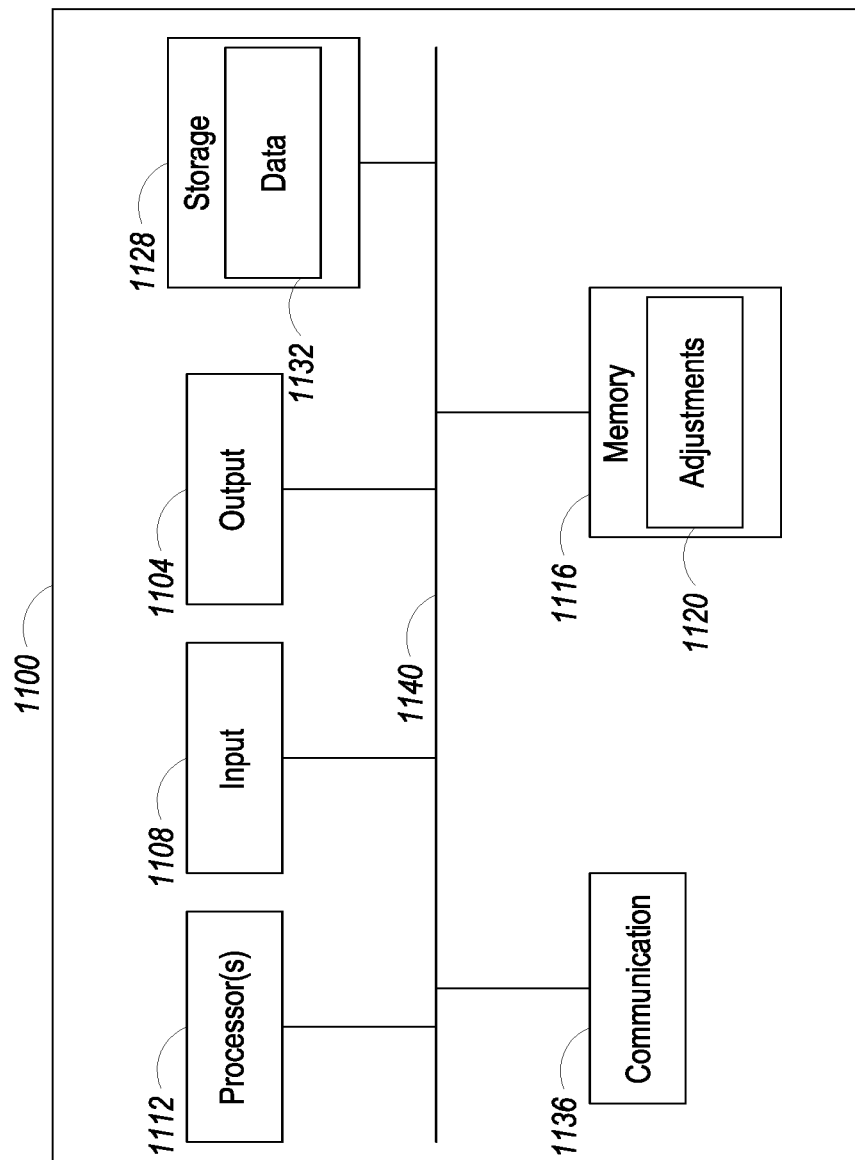
FIG. 11 illustrates a computer system on which some embodiments may be implemented.

FIG. 11 illustrates example components of a basic computer system 1100 upon which embodiments of the present invention may be implemented. For example, system 104 (FIG. 1) and/or controller 316 (FIG. 3) may incorporate features of the basic computer system 1100 shown in FIG. 11. Computer system 1100 includes output device(s) 1104, and input device(s) 1108. Output device(s) 1104 may include, among other things, one or more displays, including CRT, LCD, and/or plasma displays. Output device(s) 1104 may also include printers, speakers etc. Input device(s) 1108 may include, without limitation, a keyboard, touch input devices, a mouse, voice input device, scanners, etc.

Basic computer system 1100 may also include one or more processor(s) 1112 and memory 1116, according to embodiments of the present invention. In embodiments, the processor(s) 1112 may be a general purpose processor(s) operable to execute processor executable instructions stored in memory 1116. Processor(s) 1112 may include a single processor or multiple processors, according to embodiments. Further, in embodiments, each processor may be a single core or a multi-core processor, having one or more cores to read and execute separate instructions. The processors may include, in embodiments, general purpose processors, application specific integrated circuits (ASICs), field programmable gate arrays (FPGAs), and other integrated circuits.

The memory 1116 may include any tangible storage medium for short-term or long-term storage of data and/or processor executable instructions. The memory 1116 may include, for example, Random Access Memory (RAM), Read-Only Memory (ROM), or Electrically Erasable Programmable Read-Only Memory (EEPROM). Other storage media may include, for example, CD-ROM, tape, digital versatile disks (DVD) or other optical storage, tape, magnetic disk storage, magnetic tape, other magnetic storage devices, etc.

Storage 1128 may be any long-term data storage device or component. Storage 1128 may include one or more of the devices described above with respect to memory 1116. Storage 1128 may be permanent or removable.

Computer system 1100 also includes communication devices 1136. Devices 1136 allow system 1100 to communicate over networks, e.g., wide area networks, local area networks, storage area networks, etc., and may include a number of devices such as modems, hubs, network interface cards, wireless network interface cards, routers, switches, bridges, gateways, wireless access points, etc.

The components of computer system 1100 are shown in FIG. 11 as connected by system bus 1140. It is noted, however, that in other embodiments, the components of system 1100 may be connected using more than a single bus.

In embodiments, separation device 104 (FIG. 1), may include aspects of system 1100. In these embodiments, memory 1116 may store adjustments 1120, e.g., flow rate adjustments, centrifuge adjustments, etc. In other embodiments, storage 1128 may store data 1132 indicating, for example, a concentration of a component in a composite fluid.

It will be apparent to those skilled in the art that various modifications and variations can be made to the methods and structure of the present invention without departing from its scope. Thus, it should be understood that the invention is not limited to the embodiments given. Rather, the invention is intended to cover modifications, variations, and their equivalents.

While example embodiments and applications of the present invention have been illustrated, it is to be understood that the invention is not limited to the precise configuration shown in the figures or described above. Various modifications, changes, and variations apparent to those skilled in the art may be made in the arrangement, operation, and details of the methods and systems of the present invention disclosed herein without departing from the scope of the invention.

What is claimed is:

1. A method, comprising:
receiving, by at least one processor, first data related to a first amount of a first component in a first multi-component fluid from a first source;
determining, by the at least one processor, a first chamber flow rate based on the first data;
determining a first centrifuge speed based on the first chamber flow rate;
rotating a centrifuge at the first centrifuge speed;
introducing a first flow of a first composite fluid at the first chamber flow rate into a first separation chamber, the first composite fluid comprising at least the first component of the first multi-component fluid and a second component of the first multi-component fluid, wherein the first composite fluid is separated from the first multi-component fluid;
separating the first component of the first composite fluid from the second component of the first composite fluid by subjecting the first composite fluid while in the first separation chamber to a centrifugal field of a first strength created by the centrifuge rotating at the first centrifuge speed;
determining, by the at least one processor, a second chamber flow rate that is lower than the first chamber flow rate;
determining, based on the second chamber flow rate, a second centrifuge speed that is lower than the first centrifuge speed;
rotating the centrifuge at the second centrifuge speed;
introducing a second flow of the first composite fluid at the second chamber flow rate into the first separation chamber increasing a concentration of the first composite fluid inside the first separation chamber;
separating the first component of the first composite fluid from the second component of the first composite fluid by subjecting the first composite fluid while in the first separation chamber to a centrifugal field of a second strength created by the centrifuge rotating at the second centrifuge speed; and
collecting the first component of the first composite fluid in a first storage container.

2. The method of claim 1, wherein the first multi-component fluid comprises components of whole blood.

3. The method of claim 2, wherein the first component of the first multi-component fluid comprises platelets.

4. The method of claim 3, wherein a fluidized bed is created in the first separation chamber.

5. The method of claim 4, wherein the first separation chamber has a conical volume.

6. The method of claim 5, wherein the first separation chamber has a stepped inside surface of the conical volume.

7. The method of claim 1, wherein the first storage container stores less than $1 \times 10^6$ particles of the second component for every $3 \times 10^{11}$ particles of the first component.

8. The method of claim 1, wherein the first data corresponds to a count of platelets in the first multi-component fluid.

9. The method of claim 8, wherein the second component corresponds to white blood cells.

10. The method of claim 1, wherein the centrifugal field of the second strength is lower than the centrifugal field of the first strength.

11. The method of claim 1, wherein the first data is received from a light detector that detects light that is at least one of transmitted and reflected by the first multi-component fluid.

12. The method of claim 11, wherein prior to determining the first chamber flow rate based on the first data, the method comprises:
  determining, based on the light that is at least one of transmitted and reflected by the first multi-component fluid, a concentration of the first component in the first multi-component fluid.

13. A separation device, comprising:
  a centrifuge;
  a separation chamber mounted to the centrifuge;
  a processor coupled with the centrifuge; and
  a memory coupled with and readable by the processor and storing therein instructions that, when executed by the processor, cause the processor to:
    receive first data related to a first amount of a first component in a first multi-component fluid from a first source;
    determine a first chamber flow rate based on the first data;
    determine a first centrifuge speed based on the first chamber flow rate;
    rotate the centrifuge at the first centrifuge speed;
    introduce a first flow of a first composite fluid at the first chamber flow rate into the separation chamber, the first composite fluid comprising at least the first component of the first multi-component fluid and a second component of the first multi-component fluid, wherein the first composite fluid is separated from the first multi-component fluid;
    separate the first component of the first composite fluid from the second component of the first composite fluid by subjecting the first composite fluid while in the separation chamber to a centrifugal field of a first strength created by the centrifuge rotating at the first centrifuge speed;
    determine a second chamber flow rate that is lower than the first chamber flow rate;
    determine, based on the second chamber flow rate, a second centrifuge speed that is lower than the first centrifuge speed;
    rotate the centrifuge at the second centrifuge speed;
    introduce a second flow of the first composite fluid at the second chamber flow rate into the separation chamber increasing a concentration of the first composite fluid inside the separation chamber; and
    separate the first component of the first composite fluid from the second component of the first composite fluid by subjecting the first composite fluid while in the separation chamber to a centrifugal field of a second strength created by the centrifuge rotating at the second centrifuge speed.

14. The separation device of claim 13, wherein the instructions further cause the processor to:
  collect the first component separated from the first composite fluid in a first storage container.

15. The separation device of claim 14, further comprising:
  a tubing set comprising a tubing circuit disposed between the first source and the centrifuge.

16. The separation device of claim 15, wherein the first multi-component fluid comprises components of whole blood, and wherein the whole blood flows through at least one tubing loop of the tubing set from the first source to the centrifuge.

17. The separation device of claim 15, wherein the tubing set further comprises a cassette, wherein the first storage container is interconnected to the cassette via a conduit, and wherein the first component flows through the cassette from the separation chamber to the first storage container.

18. A method, comprising:
  receiving, by at least one processor, data related to a first concentration of a first component in a multi-component fluid from a first source;
  determining, by the at least one processor, a first chamber flow rate based on the data;
  determining a first centrifuge speed based on the first chamber flow rate;
  rotating a centrifuge at the first centrifuge speed;
  separating a first composite fluid from the multi-component fluid, the first composite fluid comprising at least one of the first component of the multi-component fluid and a second component of the multi-component fluid;
  determining, by the at least one processor, a second chamber flow rate that is lower than the first chamber flow rate;
  determining, based on the second chamber flow rate, a second centrifuge speed that is lower than the first centrifuge speed;
  rotating the centrifuge at the second centrifuge speed;
  introducing a flow of the first composite fluid at the second chamber flow rate into a separation chamber of the centrifuge increasing the first concentration to a second concentration of the first composite fluid inside the separation chamber; and
  separating the first component of the first composite fluid from the second component of the first composite fluid in the separation chamber by subjecting the first composite fluid in the separation chamber to a centrifugal field created by the centrifuge rotating at the second centrifuge speed.

19. The method of claim 18, further comprising:
  collecting, after separating, the first component of the first composite fluid in a first storage container from the separation chamber.

20. The method of claim 19, wherein the multi-component fluid comprises components of whole blood, wherein the first component of the multi-component fluid comprises platelets, and wherein the second component of the multi-component fluid comprises white blood cells.

* * * * *